United States Patent [19]

Fischer et al.

[11] Patent Number: 4,647,542
[45] Date of Patent: Mar. 3, 1987

[54] KARL FISCHER REAGENT AND METHOD FOR DETERMINING WATER BY MEANS OF THIS REAGENT

[75] Inventors: Wolfgang Fischer, Darmstadt; Karl-Dieter Krenn, Pfungstadt, both of Fed. Rep. of Germany

[73] Assignee: Merck Patent Gesellschaft mit beschränkter Haftung, Darmstadt, Fed. Rep. of Germany

[21] Appl. No.: 716,439

[22] Filed: Mar. 27, 1985

[30] Foreign Application Priority Data

Mar. 27, 1984 [DE] Fed. Rep. of Germany ....... 3411181

[51] Int. Cl.$^4$ ............................................. G01N 33/18
[52] U.S. Cl. ...................................... 436/42; 204/1 T
[58] Field of Search .................. 436/39, 42; 204/1 M, 204/1 T

[56] References Cited

U.S. PATENT DOCUMENTS

| 4,351,744 | 9/1982 | Muroi et al. | 436/42 |
| 4,416,997 | 11/1983 | Fischer et al. | 436/42 |
| 4,429,048 | 1/1984 | Schulz | 436/42 |

FOREIGN PATENT DOCUMENTS

| 0027650 | 3/1981 | Japan | 436/42 |
| 728947 | 4/1955 | United Kingdom | 436/42 |

OTHER PUBLICATIONS

Verhoff et al, Analytica Chemica Acta, 94 (1977), 395–403.

*Primary Examiner*—Arnold Turk
*Attorney, Agent, or Firm*—Millen & White

[57] ABSTRACT

A new Karl Fischer reagent contains as a pyridine substitute at least one compound of the general formula

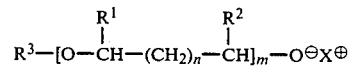

in which
$R^1$ and $R^2$, which can be identical or different, =hydrogen or alkyl having 1–6 C atoms,
$R^3$=alkyl having 1–6 C atoms,
X=alkali metal ion or one equivalent of an alkaline earth metal ion,
n=0 or a number from 1 to 4 and
m=a number from 1 to 4.

20 Claims, No Drawings

KARL FISCHER REAGENT AND METHOD FOR DETERMINING WATER BY MEANS OF THIS REAGENT

BACKGROUND OF THE INVENTION

This invention relates to a modified Karl Fischer reagent for determining water, which contains a pyridine substitute, sulfur dioxide and iodine, and to a method for determining water by means of this reagent.

The literature contains a number of proposals for replacing pyridine in the Karl Fischer reagent by other substances. In Anal. Chim. Acta 94, 395 (1977) the pyridine is replaced by sodium acetate. However, this replacement has certain disadvantages involved. Acetate esters are formed, for example with the alcohol used as the solvent, the reaction setting free water, which is of course an interferant in the method for determining water. The solutions are unstable as a result, their blank value increasing steadily.

British Pat. No. 728,947, aside from acetates, also mentions alcoholates, phenolates and metal salts of weak organic acids as replacements for pyridine. On testing the substances named in this patent, it was found that they are unsuitable replacements for pyridine, partly owing to insufficient solubility, partly owing to insufficient stability of the completed solutions. It does not take long for precipitates to form or the titer of the solution to fall drastically.

To avoid these disadvantages, a very recent proposal (European Pat: No. 35, 066) is to replace pyridine by aliphatic amines in a certain molar ratio to sulfur dioxide or by heterocyclic compounds. However, even this replacement for pyridine still has disadvantages due to the fact that the stability of the end point varies with the amount of water to be titrated. It is true that using these reagents is a way of keeping the unpleasant pyridine odor away from the user, but most of the nitrogen compounds used as replacements for pyridine are still toxic.

SUMMARY OF THE INVENTION

It thus is an object of the invention to provide a modified Karl Fischer reagent which is stable, which provides accurate analytical results, which has a very stable end point even in the case of a variable amount of water, and which is ideally of low toxicity, inter alia.

Upon further study of the specification and appended claims, further objects and advantages of this invention will become apparent to those skilled in the art.

It has been found, surprisingly, that this type of Karl Fischer reagent can be obtained by using salts of onesidedly etherified diols in place of pyridine and the state of the art replacements for pyridine.

These substances are readily soluble in the reagent solution, and said solutions are stable to storage and have stable end points even for titrating over a wide range of water levels.

These objects have thus been attained by providing a Karl Fischer reagent for determining water and containing a pyridine substitute, sulfur dioxide and iodine, wherein the pyridine substitute is at least one compound of the formula

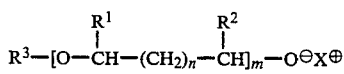

where
R$^1$ and R$^2$, which can be identical or different, =hydrogen or alkyl of 1-6 C atoms,
R$^3$=alkyl of 1-6 C atoms,
X=an alkali metal ion or one equivalent of an alkaline earth metal ion,
n=0 or a number from 1 to 4 and
m=a number from 1 to 4.

The invention also provides a method for determining water by means of this Karl Fischer reagent.

DETAILED DISCUSSION

The Karl Fischer reagent according to the invention is preferably in the form of a so-called one-component reagent, which contains all components in a single solution. This solution is sufficiently stable for use in the conventional manner as the titrating liquid. The one-component reagent is particularly advantageous whenever the substance to be analyzed is more soluble in another solvent than in the solvent of the reagent. In this case, moreover, the rate of reaction does not depend on the rate of dissolution.

It is of course also possible to use the Karl Fischer reagent according to this invention in the form of a so-called two-component reagent. This comprises two solutions, namely a dissolving agent and a titrating agent. The dissolving agent contains sulfur dioxide and the replacement for pyridine in a solvent and serves for receiving the sample to be analyzed for its water content. The titrating agent is a solution of iodine in a solvent, which has been standardized to a constant titer.

Suitable replacements for pyridine according to this invention are salts of diols etherified, on one side. They preferably have the general formula

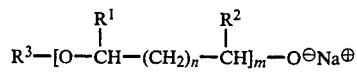

where
R1 and R2, which can be identical or different, =hydrogen or alkyl of 1-4 C atoms,
R$^3$=alkyl of 1-4 C atoms,
n=0 or 1 and
m=1 or 2.

The values of the individual parameters given above are individually preferred in general also.

Particularly preferred replacements for pyridine in the reagent according to this invention are the alkali metal and alkaline earth metal salts of ethylene glycol monomethyl ether, ethylene glycol monoethyl ether, ethylene glycol monopropyl ether and ethylene glycol monobutyl ether and of the corresponding monoalkyl ethers of 1,2- and 1,3-propanediol, of 1,2-, 1,3-, 2,3- and 1,4-butanediol, in particular salts of ethylene glycol monomethyl ether, 3-methyoxypropanol and 4-methoxybutanol. Of the salts of the derivatives of diethylene glycol and triethylene glycol, those of the monomethyl and monoethyl ethers are particularly preferred. All of these and/or their starting materials are commercially available or readily conventionally preparable.

When m is 1-4, each of the m units can independently have a value of n in the range of 0-4.

All alkyl groups in the foregoing are straight chained or branched, e.g., methyl, ethyl, or a propyl, butyl, pentyl or hexyl isomer.

To prepare the Karl Fischer reagents according to the invention, the onesidedly etherified diolates can be dissolved in a suitable solvent. The solvents are preferably the onesidedly etherified diols corresponding to the diolates. It is also particularly advantageous to prepare these solutions by dissolving a certain amount of the particular alkali metal or alkaline earth metal in one of the onesidedly etherified diols. However, the solvent need not correspond to the diolate. It can be another of these diols or another conventional Karl Fischer solvent where compatible.

The necessary amount of sulfur dioxide is then dissolved in the diolate solutions, and the resulting solution has iodine added to it as well, in the case of the so-called one-component reagents.

The molar ratio of the compound (pyridine substitute) according to the invention to sulfur dioxide should be within the range from about 1:0.7 to 1:1.5, preferably from about 1:0.9 to 1:1.2. As for the rest, the solvent for the reagent and hence the titration can in principle be any solvent described in the literature as suitable for this purpose. Similarly, all other aspects of the Karl Fischer reagent and method of this invention are conventionally determinable unless specified otherwise herein, e.g., as discussed in "Aquametry," J. Mitchell & D.M. Smith (1980) J. Wiley & Sons.

The use of the pyridine substitutes according to the invention results in a number of advantages: the change at the point of equivalence is more distinct and more stable than with conventional Karl Fischer reagents; the reagent is more soluble and consequently has a wider range of applications; it is all in all ecologically safer, less toxic, and inexpensive.

Using the Karl Fischer reagent according to the invention, the end point of the volumetric determination of water can be conventionally determined visually, photometrically or electrometrically (by the dead stop or coulometric method). The reagent is suitable for use not only in automatic titrating equipment but also for use in the open. The titration generally takes place with the exclusion of atmospheric moisture. The preferred method these days is electrometric titration, in particular the dead stop method.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

51 g of sodium is dissolved in 1 liter of ethylene glycol monomethyl ether. To this solution are added with stirring in succession 140 g of sulfur dioxide and 130 g of iodine. The sample to be analyzed for its water content is dissolved in 20 ml of ethylene glycol monomethyl ether and is titrated with the above solution. 1 ml of this solution indicates 6.5 mg of water. (Factor=6.5).

EXAMPLE 2

26 g of sodium is dissolved in 1 liter of 3-methoxypropanol. 73 g of sulfur dioxide and 65 g of iodine are added in succession with stirring. The sample to be analyzed for its water content is dissolved in 20 ml of methanol and is titrated with the above solution. The factor of this solution is 3.0.

EXAMPLE 3

52 g of sodium is dissolved in 1 liter of 4-methoxybutanol. 118 g of sulfur dioxide and 120 g of iodine are added in succession with stirring. The sample to be analyzed for its water content is dissolved in 20 ml of methanol and is titrated with the above solution. The factor of this solution is 4.5.

EXAMPLE 4

48 g of sodium is dissolved in 1 liter of diethylene glycol monoethyl ether. 110 g of sulfur dioxide and 110 g of iodine are added in succession with stirring. The sample to be analyzed for its water content is dissolved in 20 ml of methanol and is titrated with the above solution. The factor of this solution is 4.4.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A Karl Fischer reagent useful for determining water comprising effective amounts of a pyridine substitute, sulfur dioxide and iodine, wherein the pyridine substitute comprises at least one compound of the formula

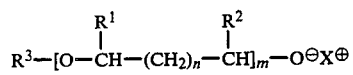

wherein
each of $R^1$ and $R^2$, which can be identical or different, is hydrogen or alkyl of 1-6 C atoms,
$R^3$ is alkyl of 1-6 C atoms,
X is an alkali metal ion or one equivalent of an alkaline earth metal ion,
n is 0 or a number from 1 to 4 and
m is a number from 1 to 4.

2. A reagent of claim 1 wherein the pyridine substitute is an alkali metal or alkaline earth metal salt of ethylene glycol monomethyl ether, ethylene glycol monoethyl ether, ethylene glycol monopropyl ether, ethylene glycol monobutyl ether or a monoalkyl ehter of 1,2- or 1,3-propanediol or of 1,2-, 1,3-, 2,3- or 1,4-butanediol.

3. In a method for determining water by means of a Karl Fischer reagent said method comprising the step of titrating a sample with a Karl Fischer reagent, the improvement wherein the reagent is one of claim 1.

4. A reagent of claim 1 wherein the pyridine substitute is an alkali metal or alkaline earth metal salt of ethylene glycol monomethyl ether, 3-methoxypropanol or 4-methoxybutanol.

5. In a method for determining water by means of a Karl Fischer reagent said method comprisng the step of titrating a sample with a Karl Fischer reagent, the improvement wherein the reagent is one of claim 4.

6. A Karl Fischer reagent of claim 1, wherein the pyridine substitute is at least one compound of the formula

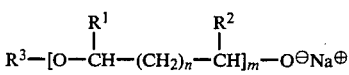

wherein
each of $R^1$ and $R^2$, which can be identical or different, is hydrogen or alkyl of 1–4 C atoms,
$R^3$ is alkyl of 1–4 C atoms,
n is 0 or 1 and
m is 1 or 2.

7. In a method for determining water by means of a Karl Fischer reagent said method comprising the step of titrating a sample with a Karl Fischer reagent, the improvement wherein the reagent is one of claim 6.

8. A reagent of claim 1 further comprising a Karl Fischer compatible solvent.

9. A reagent of claim 8 consisting essentially of said components and essentially no pyridine.

10. A reagent of claim 8 comprising a molar ratio of pyridine substitute to $SO_2$ of 1:0.7 to 1:1.5.

11. A reagent of claim 8 comprising a molar ratio of pyridine substitute to $SO_2$ of 1:0.9 to 1:1 2.

12. A reagent of claim 8 wherein $X\oplus$ is $Na^+$.

13. In a method for determining water by means of a Karl Fischer reagent said method comprising the step of titrating a sample with a Karl Fischer reagent, the improvement wherein the reagent is one of claim 8.

14. A reagent of claim 8 wherein the solvent is a diol of the formula

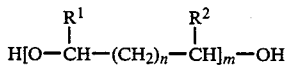

wherein $R^1$, $R^2$, n and m are as defined.

15. A reagent of claim 14 wherein the solvent diol corresponds to the pyridine substitute compound.

16. A dissolving reagent useful in a Karl Fischer titration method comprising
at least one compound of the formula

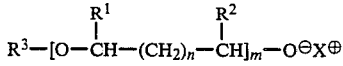

wherein
each of $R^1$ and $R^2$, which can be identical or different, is hydrogen or alkyl of 1–6 C atoms,
$R^3$ is alkyl or 1–6 C atoms,
X is an alkali metal ion or one equivalent of an alkaline earth metal ion,
n is 0 or a number from 1 to 4 and
m is a number from 1 to 4;
a Karl Fischer compatible solvent; and $SO_2$.

17. A reagent of claim 16 wherein the solvent is a diol of the formula

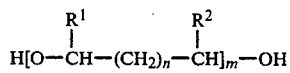

wherein $R^1$, $R^2$, n and m are as defined, and corresponds to the pyridine substitute compound.

18. A combination useful in preparing a dissolving reagent for a Karl Fischer method comprising $SO_2$ and at least one compound of the formula

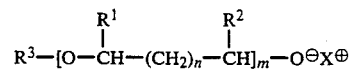

wherein
each of $R^1$ and $R^2$, which can be identical or different, is hydrogen or alkyl of 1–6 C atoms,
$R^3$ is alkyl of 1–6 C atoms,
X is an alkali metal ion or one equivalent of an alkaline earth metal ion,
n is 0 or a number from 1 to 4 and
m is a number from 1 to 4.

19. A Karl Fischer reagent system useful for determining water comprising a first solution containing a pyridine substitute and sulfur dioxide, and a second solution containing iodine in a solvent, wherein the pyridine substitute comprises at least one compound of the formula

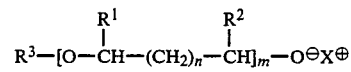

wherein
each of $R^1$ and $R^2$, which can be identical or different, is hydrogen or alkyl of 1–6 C atoms,
$R^3$ is alkyl of 1–6 C atoms,
X is an alkali metal ion or one equivalent of an alkaline earth metal ion,
n is 0 or a number from 1 to 4 and
m is a number from 1 to 4.

20. A reagent system of claim 19 wherein said first solution additionally includes and the solvent in the second solution comprises a Karl Fischer compatible solvent.

* * * * *